US 7,796,735 B2

(12) United States Patent
Yi

(10) Patent No.: US 7,796,735 B2
(45) Date of Patent: Sep. 14, 2010

(54) DETECTOR PANEL AND X-RAY IMAGING APPARATUS

(75) Inventor: Fan Yi, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 50 days.

(21) Appl. No.: 12/358,622

(22) Filed: Jan. 23, 2009

(65) Prior Publication Data

US 2009/0207974 A1    Aug. 20, 2009

(30) Foreign Application Priority Data

Feb. 15, 2008   (CN)   .................... 2008 1 0109225

(51) Int. Cl.
*H05G 1/64*    (2006.01)
*H05G 1/58*    (2006.01)

(52) U.S. Cl. .................. 378/98.8; 378/116; 250/370.09

(58) Field of Classification Search ................ 378/98.8, 378/102, 114–116, 198; 250/370.04, 370.08, 250/370.09
See application file for complete search history.

(56) References Cited

U.S. PATENT DOCUMENTS

| | | | |
|---|---|---|---|
| 4,681,227 A | 7/1987 | Tamura et al. | |
| 4,922,105 A | 5/1990 | Hosoi | |
| 5,081,543 A | 1/1992 | Romandi | |
| 5,514,873 A * | 5/1996 | Schulze-Ganzlin et al. | . 250/394 |
| 5,877,501 A * | 3/1999 | Ivan et al. | .............. 250/370.09 |
| 5,912,941 A | 6/1999 | Schmitt | |
| 6,091,982 A | 7/2000 | Reinke et al. | |
| 6,205,119 B1 | 3/2001 | Kaczynski | |
| 6,205,199 B1 * | 3/2001 | Polichar et al. | ............ 378/98.8 |
| 6,575,624 B2 | 6/2003 | Noegel et al. | |
| 6,700,126 B2 | 3/2004 | Watanabe | |
| 7,015,478 B2 * | 3/2006 | Yamamoto | ............. 250/370.09 |
| 7,078,703 B2 | 7/2006 | Watanabe | |
| 7,164,137 B2 | 1/2007 | Hayashida | |
| 7,189,972 B2 | 3/2007 | Ertel et al. | |
| 7,317,190 B2 | 1/2008 | Ertel et al. | |
| 7,342,998 B2 | 3/2008 | Kump et al. | |
| 7,396,159 B2 | 7/2008 | Utschig et al. | |
| 7,435,967 B2 | 10/2008 | Ertel et al. | |
| 2002/0150214 A1 | 10/2002 | Spahn | |
| 2009/0232278 A1* | 9/2009 | Ohara | ........................ 378/116 |

FOREIGN PATENT DOCUMENTS

| | | |
|---|---|---|
| JP | 05-079398 | 3/1993 |
| JP | 2002-336227 | 11/2002 |

\* cited by examiner

*Primary Examiner*—Edward J Glick
*Assistant Examiner*—Thomas R Artman
(74) *Attorney, Agent, or Firm*—Armstrong Teasdale LLP

(57) ABSTRACT

A detector panel having therein an X-ray detector, a signal processing circuit for interface, and a battery for power supply, the detector panel includes a first signal processing circuit for processing the detection signals from the X-ray detector, a second signal processing circuit for processing the output signal from the first signal processing circuit, a first power supply circuit for adjusting the output voltage of the battery by means of switching regulation, to supply the output to the second signal processing circuit, a second power supply circuit for adjusting the output voltage of the first power supply circuit by means of switching regulation, to supply the output to the X-ray detector and the first signal processing circuit, and a switching circuit for switching the configuration of the second power supply circuit between a single connection of one linear regulator and a series connection of two linear regulator.

20 Claims, 7 Drawing Sheets

DETECTOR PANEL AND X-RAY IMAGING APPARATUS

CROSS REFERENCE TO RELATED APPLICATIONS

This application claims the benefit of Chinese Patent Application No. 200810109225.5 filed Feb. 15, 2008, which is hereby incorporated by reference in its entirety.

BACKGROUND OF THE INVENTION

The embodiments described herein relate to a detector panel and an X-ray imaging apparatus, more specifically the present invention relates to a detector panel having therein an X-ray detector, a signal processing circuit for interface, and a battery for power supply, as well as to an X-ray imaging apparatus having such a detector panel.

There is a mobile type X-ray imaging apparatus as a sort of X-ray imaging apparatus. This type of X-ray imaging apparatus is comprised of a movable system console and a portable detector panel. The system console includes an X-ray emission device and a controller device, while the detector panel includes an X-ray detector, a signal processing circuit for interface, and a battery for power supply.

For X-ray imaging, the X-ray imaging apparatus is moved to the sickroom of a patient. To take images in the sickroom, the detector panel is placed on the imaging location of the patient, and the X-ray is emitted thereto from the opposite side. The X-ray signal, which is detected by the detector panel, is transmitted via a wired or wireless line to the system console (for example, see Japanese Unexamined Patent Publication No. 2002-336227).

In the detector panel, the power from the battery is supplied to any components requiring the power through the power supply circuit. For the power supply circuit, the circuit which consumes less power and which has a higher power supply rejection ratio (PSRR) is used. By using a circuit of less consumption of the electrical power, the durability of the battery is extended, while on the other hand by having a higher PSRR the influence of the power noise to the X-ray images is alleviated.

A power supply circuit that has a less power consumption and a higher PSRR may be comprised of a switching regulator connected in series to a linear regulator. The switching regulator contributes to the reduction of consumed power. The linear regulator contributes to the improvement of the PSRR (see, for example, Japanese Unexamined Patent Publication No. Hei 5(1993)-079398).

PSRR may have the limitation only with the linear regulator. To achieve a high PSRR desired, a plurality of linear regulators may be connected in series. However the power consumption increases as the number of linear regulator increases, as a result the battery life will last earlier.

BRIEF DESCRIPTION OF THE INVENTION

It is desirable that the problems described previously are solved.

The invention in a first aspect provides a detector panel having therein an X-ray detector, a signal processing circuit for interface, and a battery for power supply, the detector panel including: a first signal processing circuit for processing the detection signals from the X-ray detector; a second signal processing circuit for processing the output signal from the first signal processing circuit; a first power supply circuit for adjusting the output voltage of the battery by means of switching regulation, to supply the output to the second signal processing circuit; a second power supply circuit for adjusting the output voltage of the first power supply circuit by means of switching regulation, to supply the output to the X-ray detector and the first signal processing circuit; and a switching circuit for switching the configuration of the second power supply circuit between a single connection of one linear regulator and a series connection of two linear regulators.

The invention in a second aspect provides a detector panel set forth in the first aspect described above, wherein the switching circuit is responsive to relative low and high voltages in the output voltage of the first power supply circuit to perform switching to the single connection of the single linear regulator and to perform switching to the serial connection of the two linear regulators, respectively.

The invention in a third aspect provides a detector panel set forth in the second aspect described above, wherein the output voltage of the first power supply circuit is changed by switching the feedback gain of the switching regulator.

The invention in a fourth aspect provides a detector panel set forth in the third aspect described above, wherein the feedback gain is switched based on the contents of a register.

The invention in a fifth aspect provides a detector panel set forth in the fourth aspect described above, wherein the contents of the register are either the one or another of binary logic value in response to the one or another, respectively, of two operation modes of the second power supply circuit.

The invention in a sixth aspect provides a detector panel set forth in the fifth aspect described above, wherein the two operation modes are comprised of a low power consumption mode and a low noise mode.

The invention in a seventh aspect provides a detector panel set forth in the sixth aspect described above, wherein the operation modes are set through a communication.

The invention in an eighth aspect provides a detector panel set forth in the sixth aspect described above, wherein the operation modes are set manually.

The invention in a ninth aspect provides a detector panel set forth in the eighth aspect described above, which further includes a control panel for manually setting the operation modes.

The invention in a tenth aspect provides a detector panel set forth in the sixth aspect described above, which further includes a display panel for displaying the operation modes.

The invention in an eleventh aspect provides an X-ray imaging apparatus including: a system console having an X-ray emission device and a controller device; and a detector panel incorporating an X-ray detector, a signal processing circuit for interface, and a battery for power supply, the detector panel including: a first signal processing circuit for processing the detection signal of the X-ray detector; a second signal processing circuit for processing the output signal of the first signal processing circuit; a first power supply circuit for adjusting the output voltage of the battery by switching regulation, to supply the output to the second signal processing circuit; a second power supply circuit for adjusting the output voltage of the first power supply circuit by linear regulation, to supply the output to the first signal processing circuit; and a switching circuit for switching the configuration of the second power supply circuit between a single connection of one linear regulator and a series connection of two linear regulators.

The invention in a twelfth aspect provides an X-ray imaging apparatus set forth in the eleventh aspect described above, wherein the switching circuit is responsive to a relatively low and high voltage in the output voltage of the first power supply circuit to perform switching to, respectively, a single connection of the one linear regulator or a series connection of the two linear regulators.

The invention in a thirteenth aspect provides an X-ray imaging apparatus set forth in the twelfth aspect described above, wherein the output voltage of the first power supply circuit is changed by switching the feedback gain of the switching regulator.

The invention in a fourteenth aspect provides an X-ray imaging apparatus set forth in the thirteenth aspect described above, wherein the feedback gain is switched based on the contents of a register.

The invention in a fifteenth aspect provides an X-ray imaging apparatus set forth in the fourteenth aspect described above, wherein the contents of the register are either the one or the other of binary logic values in response to the one or the other, respectively, of two operation modes of the second power supply circuit.

The invention in a sixteenth aspect provides an X-ray imaging apparatus set forth in the fifteenth aspect described above, wherein the two operation modes are a low power consumption mode and a low noise mode.

The invention in a seventeenth aspect provides an X-ray imaging apparatus set forth in the sixteenth aspect described above, wherein the operation modes are set by communication.

The invention in an eighteenth aspect provides an X-ray imaging apparatus set forth in the sixteenth aspect described above, wherein the operation modes are set manually.

The invention in a nineteenth aspect provides an X-ray imaging apparatus set forth in the eighteenth aspect described above, wherein the detector panel incorporates a control panel for manually setting the operation modes.

The invention in a twentieth aspect provides an X-ray imaging apparatus set forth in the sixteenth aspect described above, wherein the detector panel incorporates a display panel for displaying the operation modes.

In accordance with the invention, in the first aspect, the detector panel which incorporates an X-ray detector, a signal processing circuit for interface, and a battery for power supply, includes: a first signal processing circuit for processing the detection signal of the X-ray detector; a second signal processing circuit for processing the output signal of the first signal processing circuit; a first power supply circuit for adjusting the output voltage of the battery by switching regulation, to supply the output to the second signal processing circuit; a second power supply circuit for adjusting the output voltage of the first power supply circuit by linear regulation, to supply the output to the X-ray detector and the first signal processing circuit; and a switching circuit for switching the configuration of the second power supply circuit between a single connection of one linear regulator and a series connection of two linear regulators. Accordingly, a detector panel capable of switching the operation between a low power consumption operation and a low noise operation is achieved.

In accordance with the invention, in an eleventh aspect, there is provided an X-ray imaging apparatus having: a system console including an X-ray emission device and a controller device; and a detector panel including an X-ray detector, a signal processing circuit for interface, and a battery for power supply, the detector panel including: a first signal processing circuit for processing the detection signal of the X-ray detector; a second signal processing circuit for processing the output signal of the first signal processing circuit; a first power supply circuit for adjusting the output voltage of the battery by switching regulation, to supply the output to the second signal processing circuit; a second power supply circuit for adjusting the output voltage of the first power supply circuit by linear regulation, to supply the output to the X-ray detector and the first signal processing circuit; and a switching circuit for switching the configuration of the second power supply circuit between a single connection of one linear regulator and a series connection of two linear regulators. Accordingly, an X-ray imaging apparatus having a detector panel capable of switching the operation between the low power consumption operation and the low noise operation can be achieved.

In accordance with the invention, in the second or twelfth aspect, the switching circuit is responsive to the relative low and high voltage in the output voltage of the first power supply circuit to perform switching to the single connection of the one linear regulator or to perform switching to the series connection of the two linear regulators, respectively, allowing adaptive switching thereby.

In accordance with the invention, in the third or thirteenth aspect, the output voltage of the first power supply circuit is changed by switching the feedback gain of the switching regulator, whereby the positive change of the output voltage is realized.

In accordance with the invention, in the fourth or fourteenth aspect, the feedback gain is switched based on the contents of a register, whereby the switching can be controlled digitally.

In accordance with the invention, in the fifth or fifteenth aspect, the contents of the register is either the one or the other of binary logic values in response to the one or the other of two operation modes of the second power supply circuit, whereby the contents of the register to be one bit is realized.

In accordance with the invention, in a sixth or sixteenth aspect, the two operation modes are the low power consumption mode and the low noise mode, allowing representing the low power consumption mode and the low noise mode by using a one bit register.

In accordance with the invention, in the seventh or seventeenth aspect, the operation modes are set by communication, whereby the setting of the operation mode can be performed remotely.

In accordance with the invention, in the eighth or eighteenth aspect, the operation modes are manually set, whereby the setting of the operation mode can be directly performed.

In accordance with the invention, in the ninth or nineteenth aspect, the detector panel has a control panel for manually setting the operation mode, allowing facilitating the manual setting of the operation modes.

In accordance with the invention, in the tenth or twentieth aspect, the detector panel has a display panel for displaying the operation modes, allowing facilitating the visual confirmation of operation modes.

Further objects and advantages of the present invention will be apparent from the following description of the preferred embodiments of the invention as illustrated in the accompanying drawings.

DETAILED DESCRIPTION OF THE INVENTION

Various embodiments of the invention will be described in greater details herein below with reference to the accompanying drawings. It should be noted here that the invention is not considered to be limited to the embodiments described herein.

Figure 1:
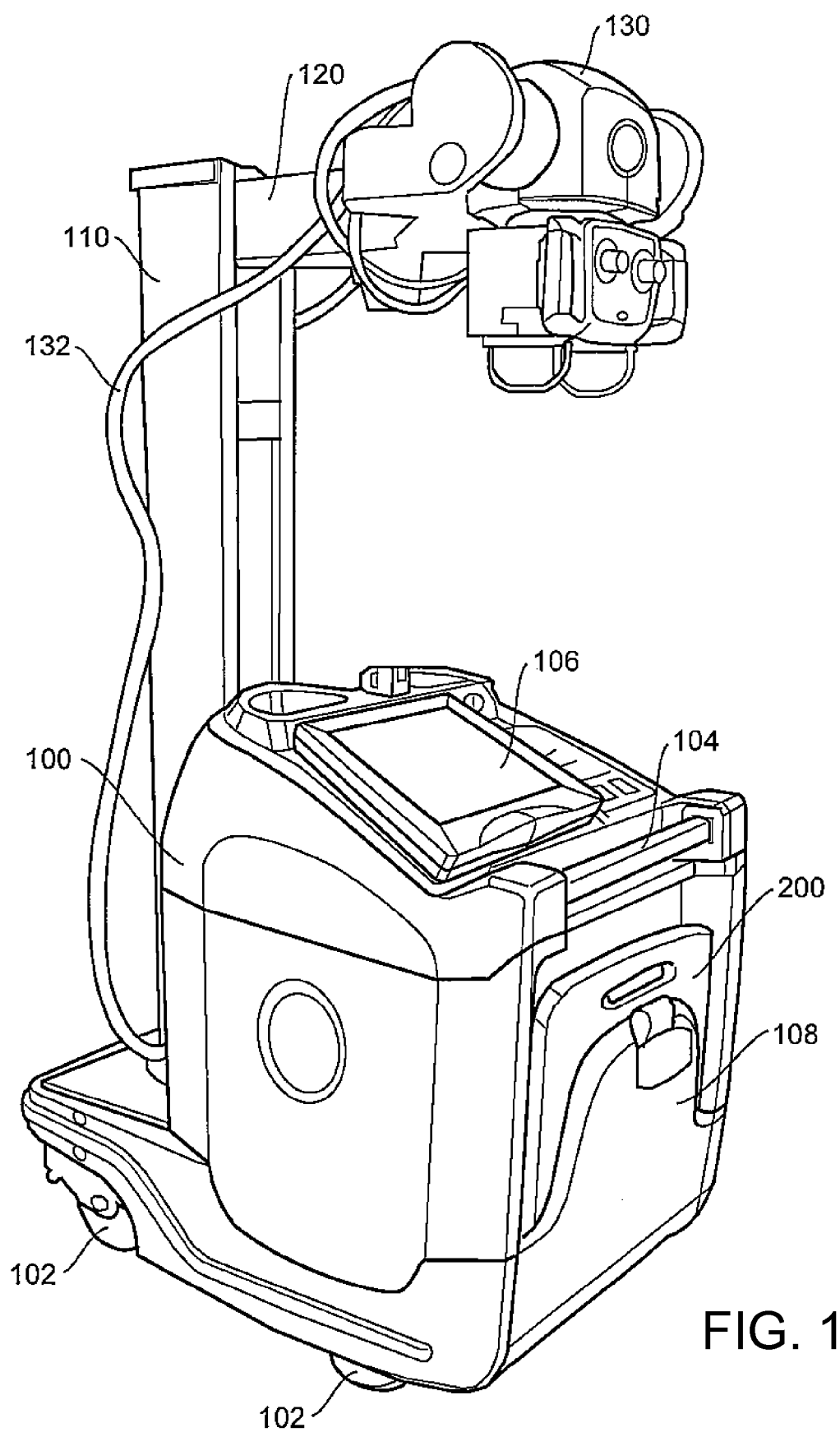
FIG. 1 is a schematic diagram illustrating the external view of an X-ray imaging apparatus.

Now referring to FIG. 1 there is shown an exterior view of an X-ray imaging apparatus. The arrangement of the present apparatus indicates one example of an X-ray imaging apparatus.

As shown in FIG. 1, the apparatus has a system console 100. The system console 100 is an example of system console embodied by the invention. The system console 100 is an approximately rectangular, box-shaped structure, which houses electronics for imaging control therein. The electronics for imaging control is an example of the control device in accordance with the invention.

Figure 2:
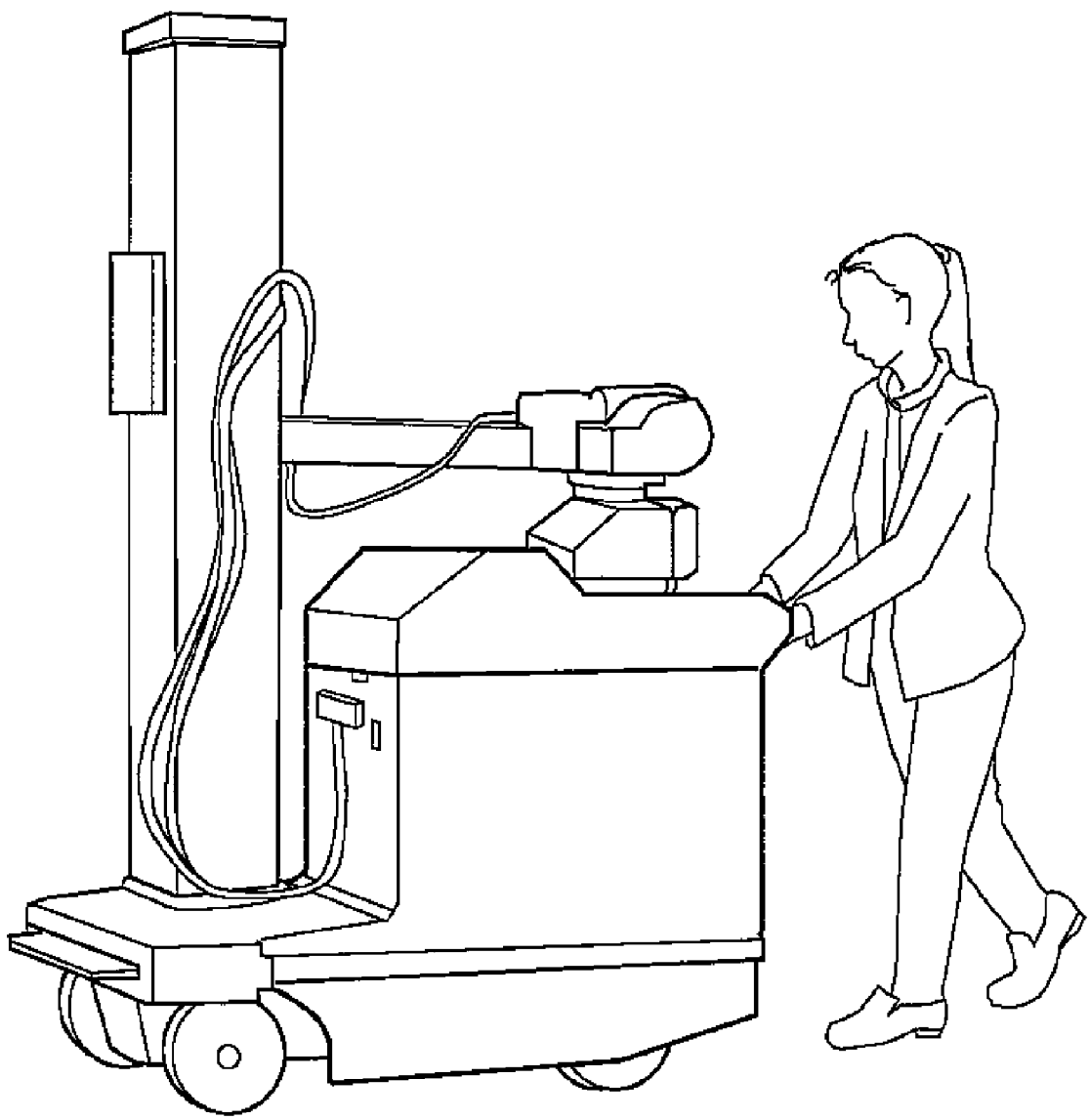
FIG. 2 is a schematic diagram illustrating the operation scene of the X-ray imaging apparatus.

The system console 100 has a caster 102 at the bottom for relocating the console, and has a handle 104 for pushing by hand. The apparatus, as shown in FIG. 2, thereby, is a mobile X-ray imaging apparatus that is capable of desirably moving to anywhere.

The top surface of the system console 100 is a control panel 106, which includes man machine communication equipment, such as for example a graphic display, a keyboard, and so on.

At the back side of the system console 100 there is provided a vertical column 110, and an X-ray emitter 130 is attached at the end of an arm 120 horizontally extending from the vertical column 110. The X-ray emitter 130 generates X-ray by using a high voltage power supplied from the system console 100 through a cable 132. The X-ray emitter 130 is an example of X-ray emission device in accordance with the invention.

The X-ray emitter 130 is capable of changing its direction at the end of the arm 120. The arm 120 is vertically movable along with the vertical column 110, which vertical column 110 swings (spins) around the longitudinal axis of the vertical column 110.

The apparatus has a detector panel 200. The detector panel 200 is an approximately square, box-shaped structure that is separated from the system console 100 so as to be portable. The detector panel 200 is housed in a storage box 108 at the front of the system console 100 when not in use, and is taken out from the storage box 108 to use when taking images.

Figure 3:
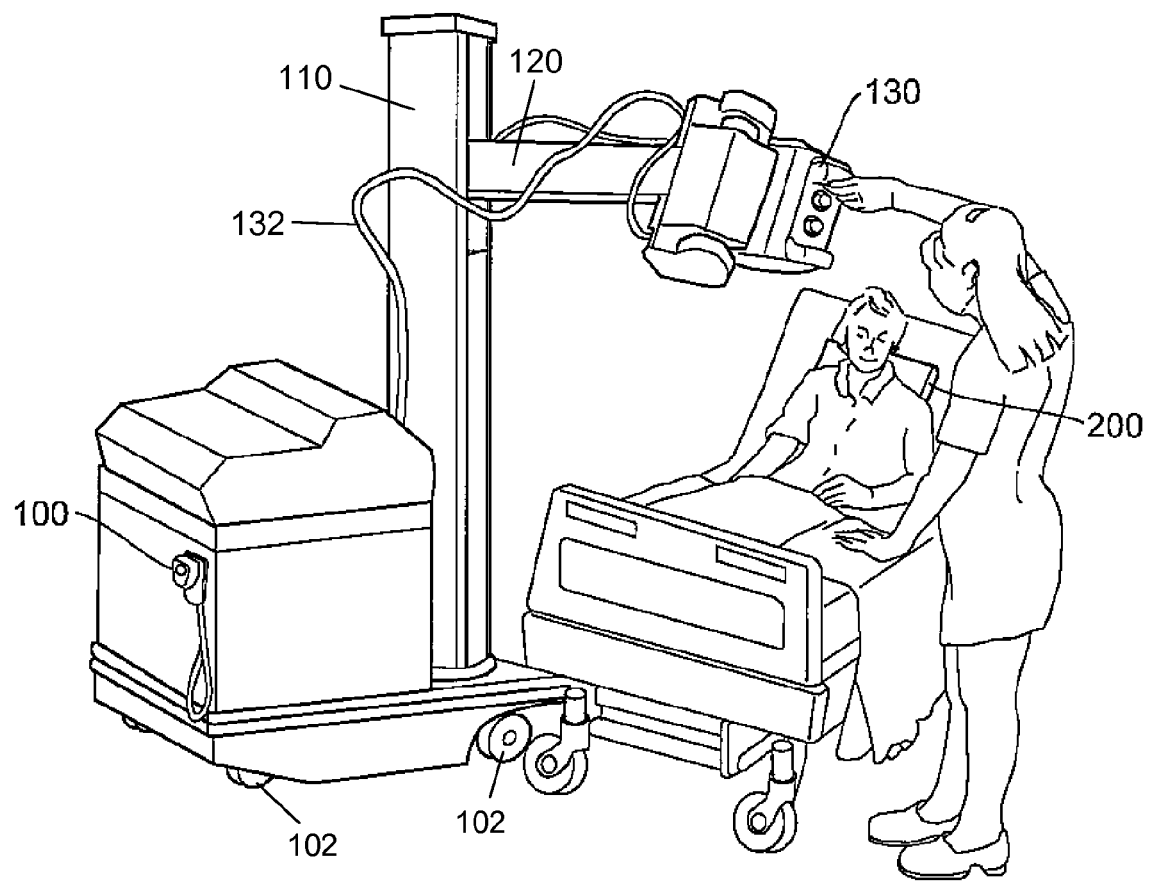
FIG. 3 is a schematic diagram illustrating the operation scene of imaging a patient by the X-ray imaging apparatus.

Now referring to FIG. 3, there is shown a schematic diagram of the apparatus in use. As shown in FIG. 3, the apparatus is operated in a sickroom. The X-ray imaging is conducted by placing the detector panel 200 for example at the back of a patient, and by emitting X-ray from the X-ray emitter 130 from the front side of the patient. The X-ray signal detected by the detector panel 200 is transmitted to the system console 100 through a wired or wireless line.

The detector panel 200 is an example of the best mode for carrying out the invention. The arrangement of the detector panel 200 indicates an example of the best mode for carrying out the invention with respect to the detector panel.

Figure 4:
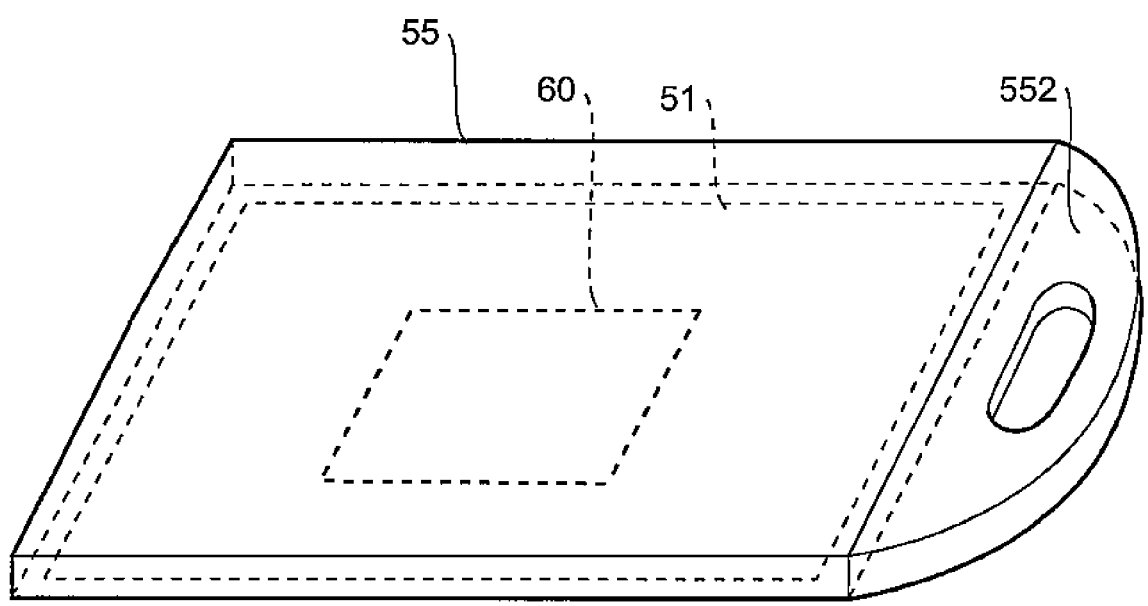
FIG. 4 is a schematic diagram illustrating the basic configuration of a detector panel.

Now referring to FIG. 4 there is shown a basic arrangement of the detector panel 200. As shown in FIG. 4, the detector panel 200 has a box-like case 55 for housing a square plate-like X-ray detector assembly 51. The case 55 has a top surface opposing to the X-ray detector plane of the X-ray detector assembly 51, which is formed by an X-ray transmissive material, and a handle 552 at one end.

In the case 55, a battery 60 for power supply is mounted at the backside of the X-ray detector assembly 51. The battery 60 is for example a secondary battery, which may be repeatedly used by recharging. The battery 60 may also be a primary battery instead of a secondary battery. The battery 60 is an example of the battery in the invention.

Figure 5:
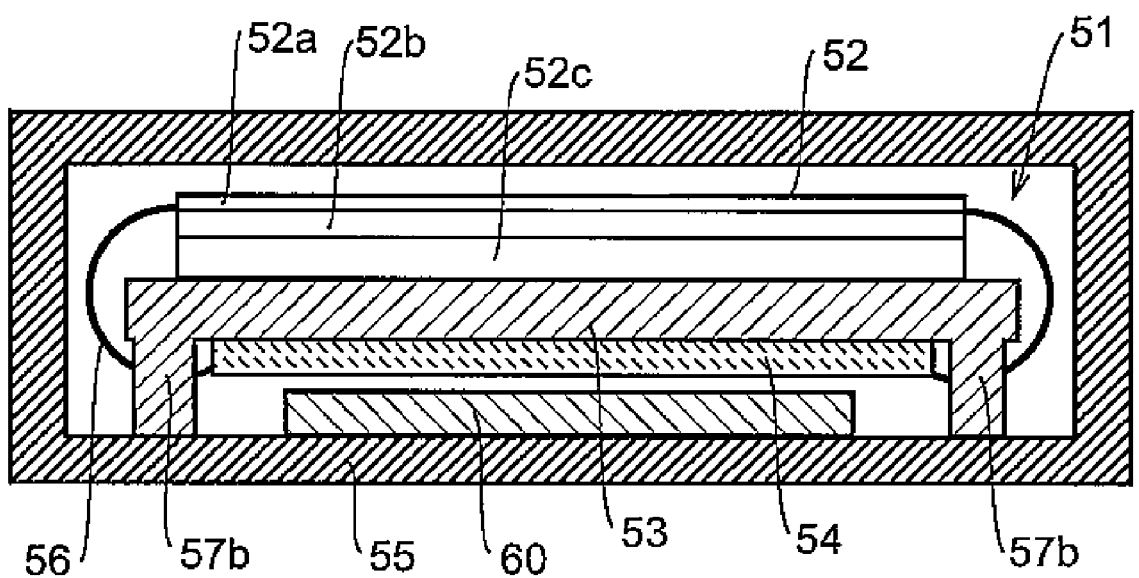
FIG. 5 is a schematic diagram illustrating the internal configuration of the detector panel.

Now referring to FIG. 5 there is shown a schematic diagram of internal arrangement of the detector panel 200. FIG. 5 shows a vertical cross sectional view of the detector panel 200. As shown in FIG. 5, the X-ray detector assembly 51 is comprised of an X-ray detector 52, a support substrate 53, and a circuit board 54. The X-ray detector 52 is mounted on a surface of the support substrate 53, the circuit board 54 is mounted on the backside surface of the support substrate 53, and the detector and the circuit board are electrically connected by a flexible circuit board 56.

The X-ray detector 52 is a laminated body formed by a scintillator layer 52a, photoelectric conversion layer 52b, and a glass substrate 52c. The scintillator layer 52a converts the X-ray into light, and the photoelectric conversion layer 52b converts the light into electric signals.

The photoelectric conversion layer 52b is made of a two-dimensional array of photoelectric conversion elements. The two-dimensional array of photoelectric conversion elements is formed as a well-known active matrix. In the active matrix, a photo diode for photoelectric conversion, a capacitor for storing the output current from the photo diode, and a thin film transistor (TFT) for outputting the charge make one unit. One unit of the active matrix corresponds to one pixel of an X-ray image.

The electric signal, which has been converted in the photoelectric conversion layer 52b, is input into the circuit board 54 through the flexible circuit board 56. There is electric circuitry equipped on the circuit board 54. The electric circuit is the interface to the system console 100, which converts input signal to digital data to transmit to the system console 100 through a wired or wireless line.

At the backside of the support substrate 53 there are four spacers formed at the four corners. A spacer 57b is integratedly formed with the support substrate 53. The support substrate 53 is self-sustained by means of the spacer 57b on the inward bottom wall of the case 55. The bottom end of the spacer 57b is fixed to the inward bottom wall of the case 55 by means of some adhesive or a screw.

Figure 6:
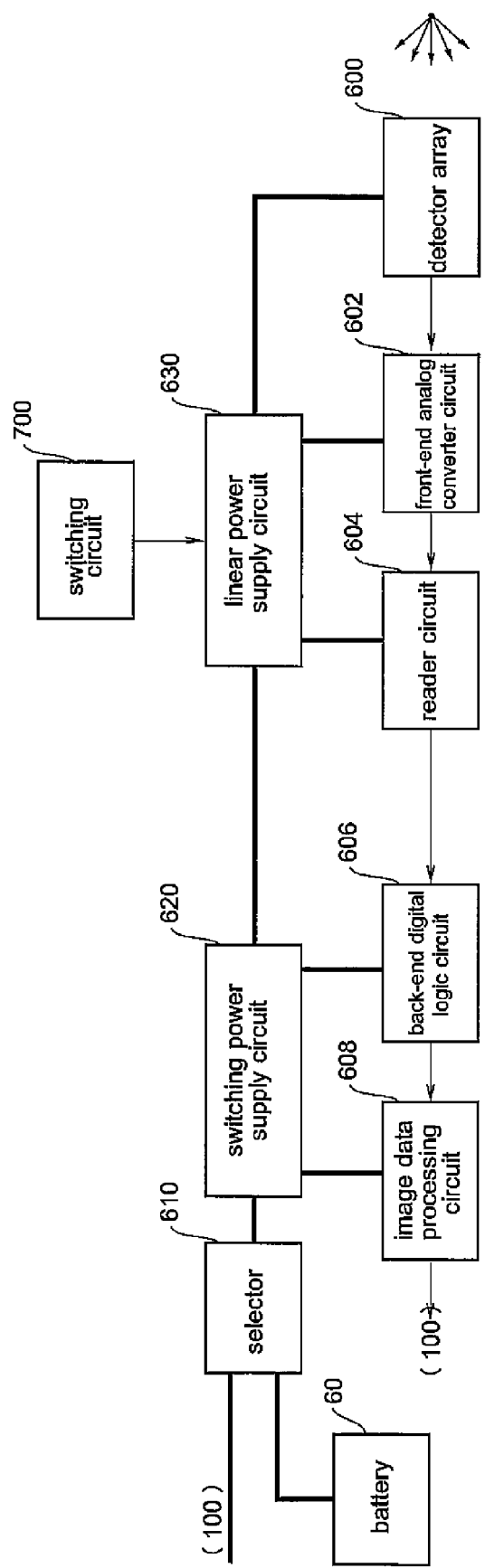
FIG. 6 is a schematic block diagram illustrating the electric configuration of the detector panel.

Now referring to FIG. 6 there is shown a schematic block diagram of electric configuration of the detector panel 200. As shown in FIG. 6 a detector array 600 detects X-ray, the detector signal is converted to a voltage signal by the front-end analog converter circuit 602, then the voltage signal is read out by the reader circuit 604.

The detector array 600 corresponds to the array made of the scintillator layer and photo diodes, and the front-end analog converter circuit 602 corresponds to the array made of capacitors, and the reader circuit 604 corresponds to the array of the TFTs. All of these circuits handle minute analog signals, and thus are susceptible to noises.

The detector array 600 is an example of the X-ray detector in accordance with the invention. The front-end analog converter circuit 602 and the reader circuit 604 are an example of the first signal processing circuit in accordance with the invention, and an example of the signal processing circuit for interfacing.

The output signal from the reader circuit 604 is digitized by a back-end digital logic circuit 606, and the digital signal thus generated constitutes an image data in an image data processing circuit 608, and then is transferred to the system console 100.

The back-end digital logic circuit 606 and the image data processing circuit 608 are both digitally signal processing circuits, which are not susceptible to noises. The back-end digital logic circuit 606 and the image data processing circuit 608 are an example of the second signal processing circuit in accordance with the invention, as well as an example of the signal processing circuit for interfacing.

The power supply voltage fed from the system console 100 or the battery 60 is input to a switching power supply circuit 620 through a selector 610. The power supplied from the system console 100 is used only when the detector panel 200 is connected to the system console 100 via wired line, and in other instances the power supplied from the battery 60 is used.

The switching power supply circuit 620 adjusts the input voltage by switching regulation to supply as power supply voltage to the back-end digital logic circuit 606 and to the image data processing circuit 608. The switching power supply circuit 620 is configured with a switching regulator. The switching power supply circuit 620 is an example of the first power supply circuit in accordance with the invention.

The output voltage of the switching power supply circuit 620 is input to a linear power supply circuit 630. The linear power supply circuit 630 adjusts the output voltage of the switching power supply circuit 620 by linear regulation to supply as power supply voltage to the detector array 600, the front-end analog converter circuit 602, and the reader circuit 604. The linear power supply circuit 630 is an example of the second power supply circuit in accordance with the invention.

The linear power supply circuit 630 is comprised of linear regulators. For the linear regulator, a low-dropout linear regulator (LDO) is used.

The linear power supply circuit 630 has two LDOs. The connection of these LDOs may be configurable as either a single connection of one LDO or a series connection of two LDOs. The switching of connection is performed by a switching circuit 700. The switching circuit 700 is an example of the switching circuit in accordance with the invention.

Figure 7:
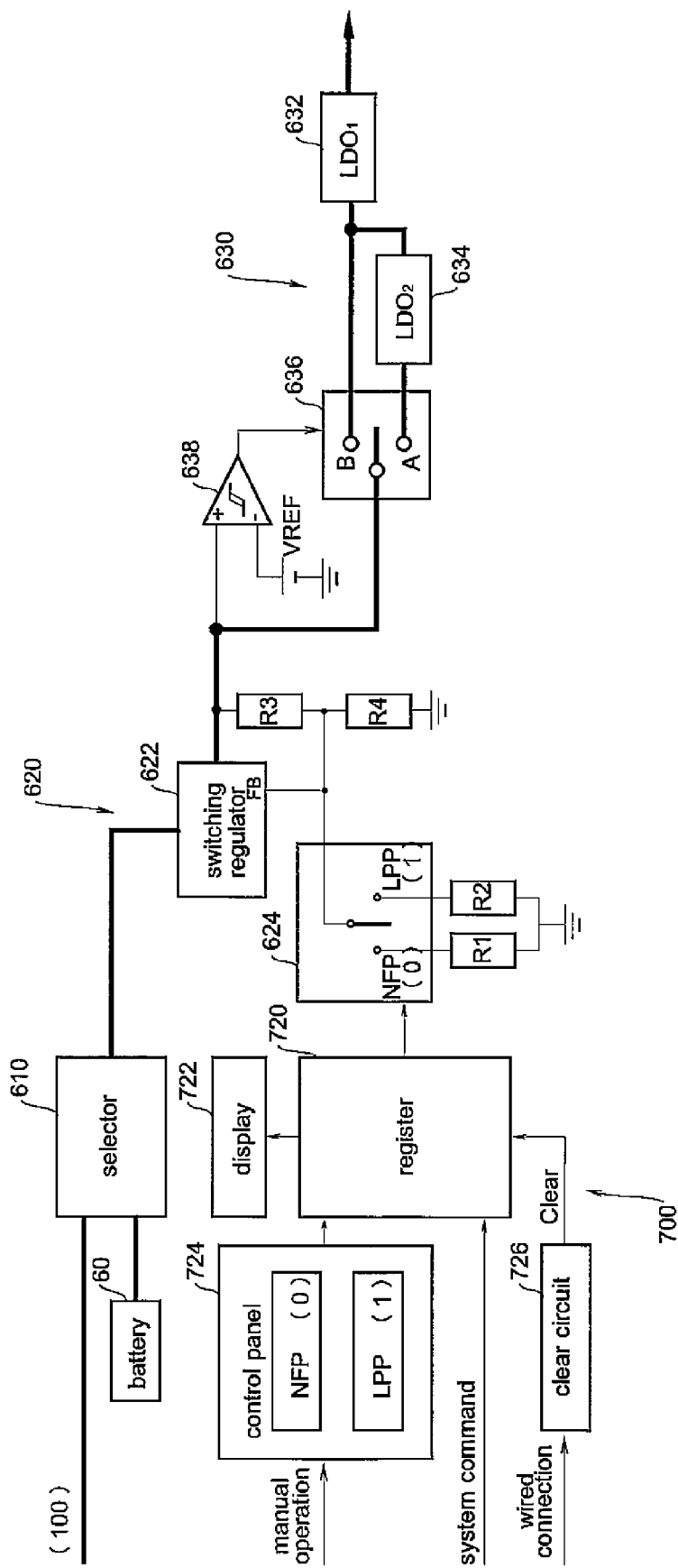
FIG. 7 is a schematic block diagram illustrating the electric configuration of a switching power supply, the linear power supply circuit, and a switching circuit.

Now referring to FIG. 7 there is shown a schematic diagram illustrating the electric configuration of the switching power supply circuit 620, the linear power supply circuit 630, and the switching circuit 700. As shown in FIG. 7 the switching power supply circuit 620 has a switching regulator 622. The output voltage of the switching regulator 622 is fed back thereto after divided by a series circuit of resistors R3 and R4.

A switch 624 connects a resistor R1 or another resistor R2 to the resistor in the ground side, R4, in parallel. The resistor R1 has a resistance value smaller than that of the resistor R2. When the resistor R1 is connected, the feedback gain decreases more than when the resistor R2 is connected, thus increases the output voltage of the switching regulator 622.

The output voltage of the switching regulator 622 varies in two step in response to the switching by the switch 624, so as to be relatively lower voltage when switched to the resister R2 side ((1) side)), while relatively higher voltage when switched to the resister R1 side ((0) side). The output voltage as such is input to the linear power supply circuit 630.

The linear power supply circuit 630 has a $LDO_1$ 632, $LDO_2$ 634, a switch 636, and a comparator 638. The $LDO_2$ 634 is the input stage LDO, and the $LDO_1$ 632 is the output stage LDO. The output voltage of the $LDO_2$ 634 is input to the $LDO_1$ 632, the output voltage of the $LDO_1$ 632 is provided to the load.

The switch 636 switches the destination of the output voltage from the switching regulator 622 to either the $LDO_1$ 632 ((B) side) or to the $LDO_2$ 634 ((A) side). When switched to (B) side, the $LDO_1$ 632 is in a single connection. When switched to (A) side, the $LDO_1$ 632 and the $LDO_2$ 634 are connected in series.

The switching by the switch 636 is performed by the comparator 638. The comparator 638 compares the output voltage of the switching regulator 622 with the reference voltage $V_{REF}$, to switch the switch 636 to (B) side if the output voltage of the switching regulator 622 is less than the reference voltage $V_{REF}$, or to switch the switch 636 to (A) side if the output voltage is higher than the reference voltage $V_{REF}$.

The reference voltage $V_{REF}$ is set so as to be the intermediate value of the output voltage from the switching regulator 622 that varies in two steps. Because of this if the output voltage of the switching regulator 622 is relatively lower voltage, then the single connection of the $LDO_1$ 632 is configured, and if the output voltage of the switching regulator 622 is relatively high voltage then the series connection of the $LDO_1$ 632 with the $LDO_2$ 634 is configured.

The output voltage of the switching regulator 622 will be relatively lower voltage when the switch 624 is switched to (1) side, and will be relatively higher voltage when the switch 624 is switched to (0) side. As a result, a single connection of $LDO_1$ 632 is configured when the switch 624 is switched to (1) side, and a series connection of $LDO_1$ 632 with the $LDO_2$ 634 is configured when the switch 624 is switched to (0) side.

The switching of the switch 624 is performed in correspondence with the contents of a register 720. The contents of the register 720 are one-bit data. The switch 624 is switched to (0) side when the one-bit logical value is [0], and is switched to (1) side when the one-bit logical value is [1].

The logical value of the one-bit data in the register 720 is displayed on a display 722. The display 722 displays either logical value [0] or [1] in accordance with either the one or the other of two display mode. As a display, a visual display device is used. As a visual display device, for example LED (light emitting diode) may be used. The display 722 is an example of the display unit in accordance with the invention.

The data in the register 720 may be manually set by a user through the control panel 724. The control panel 724 includes two keys, namely, NFP (0) and LPP (1). The control panel 724 is an example of the control panel in accordance with the invention.

NFP (0) designates to "noise free preference, (NFP)", LPP (1) designates to "low power preference, (LPP)". When the user desires the operation mode of the detector panel 200 to be low noise mode, he or she pushes the NFP (0) key to set logical value [0]. When the user desires the operation mode of the detector panel 200 to be low power mode, he or she pushes the LPP (1) to set logical value [1].

The data in the register 720 may also be configurable by a system command. A system command is supplied from the system console 100 through a communication. By using a system command the low noise mode or the low power mode may be remotely set.

The data in the register 720 may be cleared to [0] by a clear circuit 726. The data is cleared by the clear circuit 726 when the detector panel 200 is connected to the system console 100 via a wired connection.

When wired connection, the power is supplied from the system console 100 to the detector panel 200, and the power from the battery 60 is not consumed. This means that the detector panel 200 is not set to be in the low power mode. Therefore the contents of the resister should be cleared to forcibly operate in the low noise mode.

When [0] is set to the register 720 by the control panel 724 or by a system command, or when the register 720 is cleared by the clear circuit 726, the $LDO_1$ 632 and the $LDO_2$ 634 are connected in series in the linear power supply circuit 630.

In this context the PSRR of the linear power supply circuit 630 will be the product of PSRR of the $LDO_1$ 632 and PSRR of the $LDO_2$ 634, the output voltage will have very small power supply noise, i.e., voltage ripple. The detector panel will operate thereby in the low noise mode.

Such voltage is fed as the power supply voltage to the detector array 600, the front-end analog converter circuit 602, and the reader circuit 604 so that the power supply noise mixed in the front end analog signal will be so small to be neglectable. Therefore a high quality X-ray image may be obtained.

In contrast, when [1] is set in the register 720 through the control panel 724 or by a system command, in the linear power supply circuit 630 the $LDO_1$ 632 is single connected. In this context only the $LDO_1$ 632 consumes the power in the linear power supply circuit 630, so that the power consumption will decrease. The detector panel thereby operates in the low power mode to extend the battery life of the battery 60.

However, the ripple of the output voltage of the linear power supply circuit 630 will be much larger than when in the low noise mode, so that the image quality of the X-ray image will be not as good as the image quality in the low noise mode, but may be allowable as the trade-off with the extended life of the battery 60.

Many widely different embodiments of the invention may be configured without departing from the spirit and the scope of the present invention. It should be understood that the present invention is not limited to the specific embodiments described in the specification, except as defined in the appended claims.

What is claimed is:

1. A detector panel comprising:
   an X-ray detector;
   a signal processing circuit for interface;
   a battery for power supply;
   a first signal processing circuit configured to process detection signals from said X-ray detector;
   a second signal processing circuit configured to process an output signal from said first signal processing circuit;
   a first power supply circuit configured to adjust a first output voltage of said battery by means of switching regulation, to supply the first output voltage to said second signal processing circuit;
   a second power supply circuit configured to adjust a second output voltage of said first power supply circuit by means of switching regulation, to supply the second output voltage to said X-ray detector and said first signal processing circuit; and
   a switching circuit configured to switch a configuration of said second power supply circuit between a single connection of one linear regulator and a series connection of two linear regulators.

2. A detector panel according to claim 1, wherein said switching circuit is configured to respond to relative low and high voltages in the first output voltage of said first power supply circuit in order to perform switching to the single connection of said single linear regulator and to perform switching to the serial connection of said two linear regulators, respectively.

3. A detector panel according to claim 2, wherein the first output voltage of said first power supply circuit is changed by switching a feedback gain of said switching regulator.

4. A detector panel according to claim 3, wherein the feedback gain is switched based on contents of a register.

5. A detector panel according to claim 4, wherein the contents of said register are a binary logic value based on two operation modes of said second power supply circuit.

6. A detector panel according to claim 5, wherein the two operation modes include of a low power consumption mode and a low noise mode.

7. A detector panel according to claim 6, wherein the operation modes are set through a communication.

8. A detector panel according to claim 6, wherein the operation modes are set manually.

9. A detector panel according to claim 8, further comprising a control panel configured to manually set the operation modes.

10. A detector panel according to claim 6, further comprising a display panel configured to display operation modes.

11. An X-ray imaging apparatus comprising:
    a system console comprising an X-ray emission device and a controller device; and
    a detector panel comprising:
    an X-ray detector;
    a signal processing circuit interface;
    a battery for power supply;
    a first signal processing circuit configured to process detection signals from said X-ray detector;
    a second signal processing circuit configured to process an output from said first signal processing circuit;
    a first power supply circuit configured to adjust a first output voltage of said battery by means of switching regulation, to supply the first output voltage signal to said second signal processing circuit;
    a second power supply circuit configured to adjust a second output voltage of said first power supply circuit by means of switching regulation, to supply the second output voltage to said X-ray detector and said first signal processing circuit; and
    a switching circuit configured to switch a configuration of said second power supply circuit between a single connection of one linear regulator and a series connection of two linear regulators.

12. An X-ray imaging apparatus according to claim 11, wherein said switching circuit is configured to respond to a relatively low and high voltage in the first output voltage of said first power supply circuit to perform switching to, respectively, a single connection of said one linear regulator and a series connection of said two linear regulators.

13. An X-ray imaging apparatus according to claim 12, wherein the first output voltage of said first power supply circuit is changed by switching a feedback gain of said switching regulator.

14. An X-ray imaging apparatus according to claim 13, wherein the feedback gain is switched based on contents of a register.

15. An X-ray imaging apparatus according to claim 14, wherein the contents of said register are a binary logic value based on two operation modes of said second power supply circuit.

16. An X-ray imaging apparatus according to claim 15, wherein the two operation modes are a low power consumption mode and a low noise mode.

17. An X-ray imaging apparatus according to claim 16, wherein the operation modes are set by communication.

18. An X-ray imaging apparatus according to claim 16, wherein the operation modes are set manually.

19. An X-ray imaging apparatus according to claim 18, wherein said detector panel further comprises a control panel configured to manually set the operation modes.

20. An X-ray imaging apparatus according to claim 16, wherein said detector panel further comprises a display panel configured to display the operation modes.

* * * * *